United States Patent [19]

Mosbach et al.

[11] Patent Number: 4,460,509

[45] Date of Patent: Jul. 17, 1984

[54] CHEMICAL SYNTHESIS

[75] Inventors: Erwin H. Mosbach; Narayan K. N. Ayengar; Charles K. McSherry, all of New York, N.Y.

[73] Assignee: Beth Israel Medical Center, New York, N.Y.

[21] Appl. No.: 294,338

[22] Filed: Aug. 19, 1981

[51] Int. Cl.$^3$ ............................................. C07J 9/00
[52] U.S. Cl. ............................. 260/239.5; 260/397.1; 260/239.55 R
[58] Field of Search .............. 260/239.5, 239.55, 397.1

[56] References Cited

U.S. PATENT DOCUMENTS 4,180,505 12/1979 Toldy et al. ........................ 424/241

Primary Examiner—Elbert L. Roberts

[57] ABSTRACT

This invention relates to steroid compounds having a D-ring side chain structure of the formula,

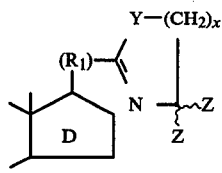

wherein $R_1$ may be $-\overset{O}{\underset{\|}{C}}-$ or $-(C_nH_{2n})-$, wherein n is an integer from 0 to 8; Y may be S, N, or O; x is and integer of from 1 to 3; and each Z may be the same or different and is selected from the group consisting of H, OH, alkyl, aryl, aralkyl, acyloxy, cycloalkyl, substituted alkyl, substituted aryl or substituted cycloalkyl.

9 Claims, No Drawings

CHEMICAL SYNTHESIS

The invention described herein was made in the course of work done under a grant or contract from the United States Department of Health and Human Services and certain rights thereto have been retained by and for the benefit of the United States Government.

This invention relates to and has as its objective the provision of steroid compounds which possess a D-ring side chain structure of the following formula:

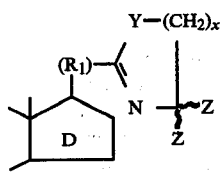

wherein $R_1$ may be

or $(C_nH_{2n})$, wherein n is an integer from 0 to 8; Y may be S, N, or O; x is an integer from 1 to 3; and each Z may be the same or different and may be H; OH; lower alkyl, straight- or branch-chained; aryl, for example, phenyl; cycloalkyl, for example, cyclobutyl, cyclopentyl, cyclohexyl or cycloheptyl; aralkyl, for example, benzyl, aryloxy; substituted lower alkyl, for example, halo-lower alkyl; substituted cycloalkyl, for example, halo-substitutedcycloalkyl; substituted aryl, for example, halo-phenyl, and substituted aralkyl, for example, halo-benzyl; and the non-toxic, pharmaceutically acceptable salts thereof. More particularly, this invention relates to and has as its objective the provision of new and useful final products which are steroids and which possess the following D-ring side-chain structure,

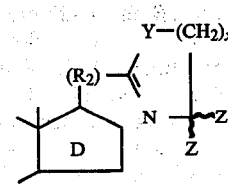

wherein $R_2$ is $-(-C_nH_{2n}-)-$, wherein n is an integer from 0 to 8; and Y, Z, and x are as hereinbefore defined.

Even more particularly, this invention relates to the provision of new and useful C-24 steroid compounds having a D-ring side chain structure of the formula:

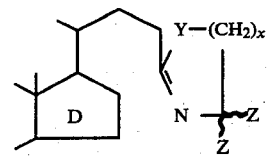

wherein Y, Z and x are as hereinbefore defined.

Even more specifically, this invention relates to and has as its objective the provision of new and useful C-24 cholane steroid compounds of the formula,

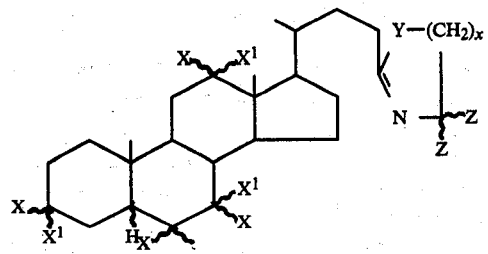

wherein each X and $X^1$ may be H; OH; acyloxy; lower alkoxy or lower alkyl, provided that when one X is OH, acyloxy or lower alkoxy, $X^1$ is H or lower alkyl; and when taken together X and $X^1$ is oxo (O=); and Y, Z and x are as hereinbefore defined.

In a preferable embodiment, this invention relates to and has as its objective the provision of C-24 cholane steroids of the formula,

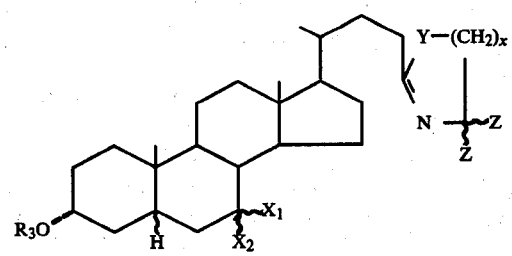

wherein $R_3$ may be H; lower alkyl, for example, methyl or ethyl; or acyl;

$X_2$ may be H; OH; acyloxy; aryloxy, lower alkyl or lower alkoxy;

$X_1$ may be H; OH; or acyloxy; provided that when $X_2$ is OH, acyloxy, aryloxy or lower alkoxy, $X_1$ is H; when taken together $X_1$ and $X_2$ may be oxo (O=); and X, Y, and Z are as hereinabove defined.

In its most preferred embodiment, the final products of this invention may be novel compounds of the formula,

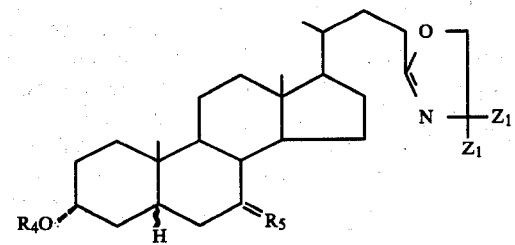

wherein $R_4$ may be H, or acyl;

$R_5$ may be selected from the group consisting of:

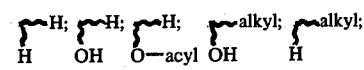

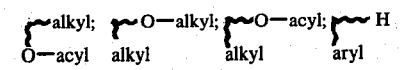

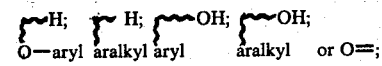

and each $Z_1$ is lower alkyl;
and the non-toxic, pharmaceutically acceptable salts thereof.

Whenever in this Specification and the claims appended thereto a wavy line ( $\wr$ ) is employed in any of the structural formulae to connect adjoining atoms, it is meant to denote that the connected moiety may be in either the alpha- or beta-stereochemical position, as the case may be.

The acyl moieties of this invention are those that are derived from hydrocarbon carboxylic acids of twelve carbon atoms or less, including such carboxylic acids as the alkanoic acids; mono-cyclic or bicyclic cycloalkanoic acids; monocyclic aryl acids, and monocyclic aralkanoic acids and other like hydrocarbons carboxylic acids.

As employed in this Specification and the claims appended hereto, the terms "alkyl" and "alkoxy" denote straight or branched chain lower alkyl or lower alkoxy moieties possessing 6 or less carbon atoms, for example, methyl or methoxy and butyl or isobutyl and butoxy.

Some of the final compounds of this invention are biologically active compounds and possess the same therapeutic activity as chenodeoxycholic acid and ursodeoxycholic acid and may be employed in the therapeutic treatment of cholesterol cholelithiasis. In addition, some of the final compounds of this invention have also been found to possess antibacterial activity and may be employed against both gram-negative and gram-positive pathogenic anaerobic bacteria.

More particularly, it has now been discovered that some of the final compounds of this invention possess substantial antibiotic activity and may be employed to combat varous bacterial microorganisms, such as, gram-positive or gram-negative anaerobic organisms, for example, certain Eubacterium and Bacteroides species. It has also been found that these final compounds possess substantial anti-bacterial properties at very low concentrations and are therefore very effective for this purpose.

The final products of this invention may be employed for the purposes thereof by administering effective amounts of said compounds to the patient being treated therewith. The route of administration of these compounds may be either parenteral or peroral. Thus, the final compounds of this invention may be administered to the patient in the form of tablets, capsules, solutions, elixirs, or compositions suitable for injection, as may be determined and selected by the skilled worker. The concentration and dosage of the final compounds which may be administered to the patient may be selected by the skilled worker depending upon the patient to whom the compound is administered as well as the condition being treated.

The novel products of this invention may be prepared in accordance with the processes of this invention which entail a number of steps beginning with a steroid starting material. The steroid starting materials which may be employed in the practice of this invention may be those which are characterized as having D-ring side chain structure of the following formula,

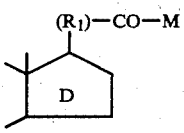

wherein $(R_1)$ may be

or $-(C_nH_{2n})-$,
wherein n is an integer from 0 to 8; and
wherein M may be OH; alkoxy, for example, methoxy or ethoxy; or halogen, for example, chloro.

The steroid starting materials which may be employed in the practice of the instant invention include such steroids as the derivatives and analogs of the pregnan-21-oic acids; the cholestan-27-oic acids; the cholan-24-oic acids or the androstan-17-carboxylic acids. More particularly, among the starting materials which may be employed in the practice of the instant invention may be those which contain a free carboxylic acid group in their D-ring side chains and which include such compounds as: cholanoic acid; 3-hydroxycholanic acids, for example, lithocholic acid; 7α-hydroxycholanic acid; 3,7-dihydroxycholanic acid, for example, chenodeoxycholic acid or ursodeoxycholic acid; 3,6-dihydroxycholanic acid, for example, hyodeoxycholic acid; 3,12-dihydroxycholanic acid, for example, deoxycholic acid, 3,7,12-trihydrox cholanic acids, for example, cholic acid; 3,6,7-trihydroxycholanic acids, for example, hyocholic acid, the muricholic acids; pythocholic acid; bitocholic acid; ketocholanoic acid, for example, 3-ketocholanoic acid, 7-hydroxy-3-ketocholanoic acid, 3-hydroxy-6-ketocholanoic acid, 12-hydroxy-3-ketocholanoic acid, 7-ketolithocholic and 12-ketolithocholic acid, 3,12-diketocholanic acid, 3m7,12-triketocholanic acid, 7-ketodeoxycholic acid; or 3-ketochola-4:6-dienic acid; allocholic acid; allodeoxycholic acid; 23,24-dinor-5β-cholan-22-oic acid; 24-nor-5β-cholan-23-oic acid; 5β-androstane-17-carboxylic acid; 25-homo-5β-cholan-25-oic acid; 25,26-dihomo-5β-cholan-25-oic acid; 5β-cholestan-26-oic acid; and other like steroids. It should also be understood that the starting materials employable in the practice of this invention may be otherwise substituted in various positions in the molecule for example, by acyl, alkyl, halo and other like substituents without effecting the final products of this invention except that those final products will retain corresponding substitutents at corresponding positions on the molecule. In addition, the steroid starting materials useful in the practice of this invention may be saturated compounds or may be unsaturated for example, $\Delta^1$, $\Delta^4$, $\Delta^5$, $\Delta^{9(11)}$, and $\Delta^{11}$ steroid compounds may be employed, with the resultant final products likewise retaining said double bond in the corresponding position on the molecule. All of the starting materials of the instant invention are known compounds and may be prepared in accordance with the disclosures and procedures set forth in the prior art, which may be easily located and determined by the skilled worker by reference to Chemical Abstracts or such other reference source as may be considered sufficient.

In its most preferable embodiment, the instant invention may be practiced with a cholan-24-oic acid starting material, for example, lithocholic acid, cholic acid, chenodexoycholic acid or ursodeoxycholic acid. The processes of the instant invention may be illustrated by the following equations employing the 3,7-dihydroxycholanoic acids as starting materials, although the other starting materials may also be satisfactorily employed yielding corresponding results:

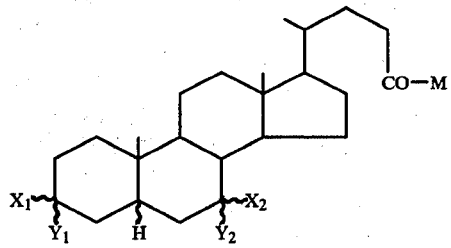

A

I. $X_1=Y_1=X_2=Y_2=H$; $M=OH$
II. $X_1=Y_1=H$; $X_2+Y_2=O=$; $M=OH$
III. $X_1=X_2=OH$; $Y_1=Y_2=H$; $M=OH$
IV. $X_1=X_2=O-Acyl$; $Y_1=Y_2=H$; $M=OH$
V. $X_1=X_2=O-Acyl$; $Y_1=Y_2=H$; $M-Cl$
VI. $X_1=X_2=O-Acyl$; $Y_1=Y=H$; $M=OCH_3$ $+Q_1-W-Q_2\rightarrow$

B

VII $Q_1=NH_2$; $W=CH_2$; $Q_2=CH_2OH$
VIII $Q_1=NH_2$; $W=C(CH_3)_2$; $Q_2=(CH_2)_2-CH_2OH$
IX. $Q_1=NH_2$; $W=C(CH_3)_2$; $Q_2=CH_2OH$
X. $Q_1=NH_2$; $W=C(CH_3)_2$; $Q_2=CH_2-CH_2OH$
XI. $Q_1=NH_2$; $W=C(C_6H_5)_2$; $Q_2=CH_2OH$
XII. $Q_1=SH$; $W=C(CH_3)_2$; $Q_2=CH_2-NH_2$
XIII. $Q_1=NH_2$; $W=C(CH_3)_2$; $Q_2=CH_2-SH$
XIV. $Q_1=NH_2$; $W=C(CH_3)_2$; $Q_2=CH_2-NH_2$
XV. $Q_1=NH_2$; $W=C(CH_3)_2$; $Q_2=CH_2-CH_2-OH$
XVI. $Q_1=NH_2$; $W=C(CF_3)_2$; $Q_2=CH_2OH$
XVII. $Q_1=NH_2$; $W=C(C_6H_{11})_2$; $Q_2=CH_2OH$
XVIII. $Q_1=NH_2$; $W=CH_2$; $Q_2=COOH$
XIX. $Q_1=NH_2$; $W=C(CH_3)_2$; $Q_2=COOH$

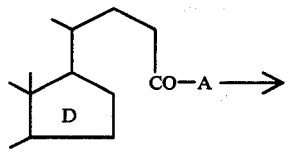

C

VIIa. $A=NHCH_2CH_2OH$
VIIIa. $A=NHC(CH_3)_2(CH_2)_2CH_2OH$
IXa. $A=NHC(CH_3)_2CH_2OH$
Xa. $A=NHC(CH_3)_2CH_2CH_2OH$
XIa. $A-NHC(C_6H_5)_2CH_2OH$
XIIa. $A=SC(CH_3)_2CH_2NH_2$
XIIIa. $A=NHC(CH_3)_2CH_2SH$
XIVa. $A-NHC(CH_3)_2CH_2NH_2$
XVa. $A=NHC(CH_3)_2CH_2CH_2OH$
XVIa. $A=NHC(CF_3)_2CH_2OH$
XVIIa. $A=NHC(C_6H_{11})_2CH_2OH$
XVIIIa. $A=NHCH_2COOH$
XIXa. $A=NHC(CH_3)_2COOH$

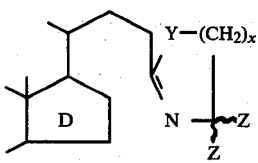

D

VIIb. $Y=O$; $x=1$; $Z=H$
VIIIb. $Y=O$; $x=3$; $Z=CH_3$
IXb. $Y=O$; $x=1$; $Z=CH_3$
Xb. $Y=O$; $x=2$; $Z=CH_3$
XIb. $Y=O$; $x=1$; $Z=C_6H_5$
XIIb. $Y=N$; $x=2$; $Z=CH_3$
XIIIb. $Y=S$; $x=2$; $Z=CH_3$
XIVb. $Y=N$; $x=2$; $Z=CH_3$
XVb. $Y=O$; $x=2$; $Z=CH_3$
XVIb. $Y=O$; $x=1$; $Z=CF_3$
XVIIb. $Y=O$; $x=1$; $Z=C_6H_{11}$

In accordance with the processes of the instant invention, the starting material may first be treated in such a way as to protect any reactive substituents which may be desired to be retained, prior to further treatment to obtain the desired final products of the instant invention. Thus, where the 3,7-dihydroxy compounds are the starting materials, they may be treated by suitable acylating agents to yield the 3,7-diacyloxy compounds, as is a well known practice in the art. The thus protected compounds may then be treated with a suitable halogenating agent, such as, thionyl chloride, phosphoryl chloride or oxalyl chloride, to yield the carbonyl halide compounds. These carbonyl halide compounds may then be reacted with a suitable reagent of the formula:

$$Q_1-(W)-Q_2$$

wherein $Q_1$ is $NH_2$ or SH;

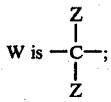

wherein each Z is the same or different and may be H; lower alkyl; e.g., methyl or ethyl; cycloalkyl; e.g., cyclohexyl; aryl, e.g., phenyl; aralkyl, e.g., benzyl; haloalkyl, e.g., $CF_3$; or haloaryl, e.g., chlorophenyl; and $Q_2$ is $(CH_2)_r-Q_4$; wherein r is an integer from 0 to 3; and $Q_4$ may be $-COOH$; $-CH_2OH$, $-SO_3H$; $-SH$ or $-NH_2$.

As can be seen from the foregoing reaction formulae, treatment of Compounds A with Compounds B yield Compounds C, having the D-ring side chain structures set forth in said formulae, Compounds C (VIIa–XVIIa). (For convenience, only the D-rings and their side chains of Compounds C and D are depicted in the formulae, the remainder of the molecule corresponding to the compound being processed.)

These intermediate Compounds C may then be reacted with suitable cyclizing agents, for example, thionyl chloride, followed by treatment with a suitable base, such as sodium hydroxide or sodium bicarbonate, to yield the corresponding heterocyclic derivatives (Compounds D), which are also novel final products of the instant invention.

It should be understood that the various other final products of this invention which may be steroid compounds with various other substituents at various other positions on their molecule or possessing various unsaturations, i.e., double bonds at various positions, may be obtained by following the same procedures as herein set forth except for the substitution of other corresponding starting materials for those described herein, all as is well known to and appreciated by the skilled worker.

The invention may be further illustrated by the following examples:

EXAMPLE 1

3α-Formyloxy-5β-cholan-24-oic Acid

Ten grams of lithocholic acid was dissolved in 40 ml. of 89.9% formic acid and 8 drops of 70% perchloric acid, and the resulting solution heated to 55° C. with stirring. The solution was then cooled to 40° C. at which time 35 ml. of acetic anhydride was slowly added and the temperature of the reaction mixture maintained between 55°–60° C. The solution was cooled and poured into 500 ml. of water and the resulting precipitate was filtered, washed with water and dried to yield 3α-formyloxy-5β-cholan-24-oic acid.

EXAMPLE 2

3α,7α,12α-triformyloxy-5β-cholan-24-oic acid; 3α,7α-diformyloxy-5β-cholan-24-oic acid; 3α-formyloxy-7-keto-5β-cholan-24-oic acid; 3α,7β-diformyloxy-5β-cholan-24-oic acid.

The procedures of Examples 1 are followed except that equivalent amounts of cholic acid; chenodeoxycholic acid; 7-ketolithocholic acid; and ursodeoxycholic acid are respectively substituted for lithocholic acid to yield, respectively, 3α,7α,12α-triformyloxy-5β-cholan-24-oic acid; 3α,7α-diformyloxy-5β-cholan-24-oic acid; 3α-formyloxy-7-keto-5β-cholan-24-oic acid; 3α,7β-diformyloxy-5β-cholan-24-oic acid.

EXAMPLE 3

3α-Formyloxy-5β-cholan-24-oyl chloride

To a solution of 10 grams of 3α-formyloxy-5β-cholan-24-oic acid in 100 ml. of benzene was added dropwise 15 ml. of thionyl chloride and the mixture was then evaporated to dryness in vacuo and the excess thionyl chloride removed by distilling twice with 50 ml. of benzene, leaving 3α-formyloxy-5β-cholan-24-oyl chloride.

EXAMPLE 4

3α,7α-Diformyloxy-5β-cholan-24-oyl chloride; 3α,7β-diformyloxy-5β-cholan-24-oic acid; 3α-formyloxy-7-keto-5-cholan-24-oyl chloride Following the procedures of Example 3 but substituting equivalent amounts of 3α,7α-diformyloxy-5β-cholan-24-oic acid; 3α,7β-diformyloxy-5β-cholan-24-oic acid; or 3α-formyloxy-7-keto-5β-cholan-24 oic acid for the 3α-formyloxy-5β-cholan-24-oic acid there is obtained respectively, 3α,7α-Diformyloxy-5β-cholan-24-oyl chloride; 3α,7β-diformyloxy-5β-cholan-24-oic acid; 3α-formyloxy-7-keto-5β-cholan-24-oyl chloride.

EXAMPLE 5

2-(3α-Formyloxy-5β-cholan-24-amido)-2-methyl-1-propanol

A solution of 10 grams of 3α-formyloxy-5β-cholan-24-oylchloride in 40 ml. of dry dichloromethane was added dropwise to a solution of 4.25 gm. of 2-amino-2-methyl-1-propanol in 10 ml. of dichloromethane at 0° C. After one hour the reaction mixture was filtered and the precipitate was washed with dichloromethane and the combined filtrate and washing thus obtained were then evaporated to dryness, yielding a crude residue, which was then purified by column chromotography on silica gel. The purified material was eluted with chloroform and chloroform-acetone (95:5) to yield 2-(3α-formyloxy-5β-cholanic-24-amido)-2-methyl-1-propanol;

m.p.=153°–155° C., $[\alpha]_D=38.6°$; $C_{29}H_{49}O_4N$: Calc: C, 73.2; H, 10.31; N, 2.94 Found: C, 73.9; H, 10.52; N, 2.79

EXAMPLE 6

Similarly, following the procedures of Example 5, but substituting equivalent amounts of the compounds in Column 1 below, for the 2-amino-1-methyl-1-propanol there are obtained the corresponding Compounds C, (as set forth hereinabove) wherein A has the value set forth in Column 2:

| Column 1 | Column 2 (A=:) |
|---|---|
| 2-amino-2-ethyl-1-butanol | —NHC(C$_2$H$_5$)$_2$CH$_2$OH |
| 2-amino-2,2-diphenyl-1-ethanol | —NHC(C$_6$H$_5$)$_2$CH$_2$OH |
| 2-amino-2,2-cyclohexyl-1-ethanol | —NHC(C$_6$H$_{11}$)$_2$CH$_2$OH |
| 2-amino-2,2-trifluoromethyl-1-ethanol | —NHC(CF$_3$)$_2$CH$_2$OH |
| 2-aminopropyl-2-sulfonic acid | —NHC(CH$_3$)$_2$SO$_3$H |
| ethanolamine | —NHCH$_2$CH$_2$OH |

EXAMPLE 7

2(3α,7α-Diformyloxy-5β-cholan-24-amido)-2-methyl-1-propanol; 2-(3α,7β-diformyloxy-5β-cholan-24-amido)-2-methyl-1-propanol; or 2-(3α-formyloxy-7-keto-5β-cholan-24-amido)-2-methyl-1-propanol Following the procedures set forth in Example 5, but substituting equivalent amounts of 3α,7α-diformyloxy-5β-cholan-24-oyl chloride, or 3α,7β-diformyloxy-5β-cholan-24-oyl chloride; or 3α-formyloxy-7keto-5β-cholan-24-oyl chloride, for 3α-formyloxy-5β-cholan-24-oyl chloride there is obtained respectively 2-(3α,7α-Diformyloxy-5β-cholan-24-amido)-2-methyl-1-propanol; 2-(3α,7β-diformyloxy-5β-cholan-24-amido)-2-methyl-1-propanol; or 2-(3α-formyloxy-7-keto-5β-cholan-24-amido)-2-methyl-1-propanol.

EXAMPLE 8

2-(3α-Hydroxy-7-keto-5β-cholan-24-amido)-2-methyl-1-propanol

To 10 grams of 2-(3α-formyloxy-7-keto-5β-cholan-24-amido)-2-methyl-1-propanol in 300 ml. of acetone was added dropwise, 200 ml. of 0.2N sodium hydroxide over a period of 30 minutes and the mixture was then permitted to stand for 1 hour. One liter of water was added to yield white crystals which were then filtered washed with water, dried and recrystallized from chloroform-acetone to obtain 2-(3α-hydroxy-7-keto-5β-cholan-24-amido)-2-methyl-1-propanol.

m.p.=220°–222° C.; $[\alpha]_D=-23.4°$; $C_{28}H_{47}H$: Calc. C, 72.9; H, 10.19; N, 3.03 Found: C, 72.1; H, 9.94; N, 3.02

EXAMPLE 9

2-(3α-Formyloxy-24-nor-5β-cholanyl)-4,4-dimethyl-2-oxazoline

In 50 ml. of dry tetrahydrofuran was dissolved 10 grams of 2-(3α-formyloxy-5β-cholan-24-amido)-2-methyl-1-propanol and the solution was then cooled to 0° C. 8 ml. of ice-cold, thionyl chloride was then added dropwise and the reaction mixture was allowed to stand at 0° C., for 1 hour after which it was slowly added to 500 ml. of ether causing a precipitate to form. After filtration, washing with ether and drying, the resultant residue was then suspended in ether to which was added a saturated solution of sodium bicaronate, the resulting ether layer washed to neutrality and dried. The ether layer was then evaporated to yield 2(3α-formyloxy-24-nor-5β-cholanyl)-4,4-dimethyl-2-oxazoline.

m.p.=108°-109° C.; $[\alpha]_D = +40.8°$ $C_{29}H_{41}O_3N$: Calc. C, 76.1; H, 10.28; N, 3.06 Found: C, 76.5; H, 10.46; N, 3.06

EXAMPLE 10

2-(3α,7α-Diformyloxy-24-nor-5β-cholanyl)-4,4-dimethyl-2-oxazoline; 2-(3α,7β-diformyloxy-24-nor-5β-cholanyl)-4,4-dimethyl-1,2-oxazoline; 2-(3α-formyloxy-7-keto-24-nor-5β-cholanyl)4,4-dimethyl-2-oxazoline Following the procedure set forth in Example 9 but substituting equivalent amounts of 2-(3α,7α-diformyloxy-5β-cholan-24-amido)-2-methyl-1-propanol or 2-(3α,7β-diformyloxy-5β-cholan-24-amido)-2-methyl-1-propanol, or 2-(3α-formyloxy-7-keto-5β-cholan-24-amido)-2-methyl-1-propanol for the 2-(3α-formyloxy-5β-cholan-24-amido)-2-methyl-1-propanol, there is obtained, respectively 2-(3α,7α-Diformyloxy-24-nor-5β-cholanyl)-4,4-dimethyl-2-oxazoline, 2-(3α,7β-diformyloxy-24-nor-5β-cholanyl)-4,4-dimethyl-2-oxazoline; 2-(3α-formyloxy-7-keto-24-nor-5β-cholanyl)-4,4-dimethyl-2-oxazoline.

EXAMPLE 11

2-(3α-Hydroxy-24-nor-5β-cholanyl)-4,4-dimethyl-2-oxazoline

Ten grams of 2-(3α-formyloxy-24-nor-5β-cholanyl)-4,4-dimethyl-2-oxazoline was refluxed for 2 hours with 100 ml. of 2% methanolic sodium hydroxide. The reaction mixture was then cooled and diluted with water to yield crystals which were filtered, washed and dried and upon recrystallization yielded 2-(3α-hydroxy-24-nor-5β-cholanyl)-4,4-dimethyl-2-oxazoline.

m.p.=149°-150° C.; $[\alpha]_D = +30.4°$; $C_{28}H_{47}O_2N$ Calc: C, 78.3; H, 10.95; N, 3.26 Found: C, 78.5; H, 10.28; N, 3.07

EXAMPLE 12

2-(3α,7α-Dihydroxy-24-nor-5β-cholanyl)-4,4-dimethyl-2-oxazoline; 2-(3α,7β-dihydroxy-24-nor-5β-cholanyl)-4,4-dimethyl-2-oxazoline; 2(3α-hydroxy-7-keto-24-nor-5β-cholanyl)-4,4-dimethyl-2-oxanzoline Following the procedure set forth in Example 11 but substituting equivalent amounts of 2-(3α,7α-diformyloxy-24-nor-5-cholanyl)-4,4-dimethyl-2-oxazoline, or 2-(3α,7β-diformyloxy-24-nor-5β-cholanyl)-4,4-dimethyl-2-oxazoline or 2-(3α-formyloxy-7-keto-24-nor-5β-cholanyl)-4,4-dimethyl-2-oxazoline for 2-(3α-formyloxy-24-nor-5β-cholanyl)4,4-dimethyl-2-oxazoline there are obtained, respectively, 2-(3α,7α-Dihydroxy-24-nor-5β-cholanyl)-4,4-dimethyl-2-oxazoline; 2-(3α,7β-dihydroxy-24-nor-5β-cholanyl)-4,4-dimethyl-2-oxazoline; 2-(3α-hydroxy-7-keto-24-nor-5β-cholanyl)-4,4-dimethyl-2-oxazoline.

EXAMPLE 13

2-(3α,7ξ-dihydroxy-7ξ-methyl-24-nor-5β-cholanyl)-4,4-dimethyl-2-oxazoline

Into 240 ml. of dry benzene was dissolved 15 grams of 2-(3α-hydroxy-7-keto-24-nor-5β-cholanyl)-4,4-dimethyl-oxazoline and the resultant solution was added dropwise to a 2.2M solution of 60 ml. of methyl magnesium iodide and 60 ml. of benzene, over a period of 30 minutes. The reaction mixture was refluxed for a period of 6 hours and left at room temperature overnight. A saturated solution of ammonium chloride was added to the reaction mixture which was then extracted exhaustively with benzene. The benzene extract was then washed to neutrality, dried and evaporated to dryness to yield a colorless oily residue of 2-(3α,7ξ-dihydroxy-7ξ-methyl-24-nor-5β-cholanyl)-4,4-dimethyl-2-oxazoline.

The foregoing examples should only be considered illustrative of the instant invention. The skilled worker is fully aware and capable of substituting other reactants for those employed in the Examples to obtain corresponding compounds. Thus, for instance, those C-24 cholane compounds which possess various substituents, such as halo, keto, alkyl or trifluoromethyl, at various positions in the molecule may easily be employed in the practice of the instant invention to obtain the corresponding desired end products.

The invention may be variously otherwise encompassed within the scope of the appended claims.

What is claimed is:

1. A steroid compound of the pregnane, cholestane, cholane or androstane series having a D-ring side chain structure of the formula:

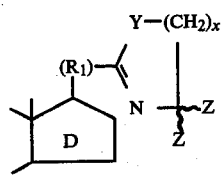

wherein $R_1$ is

or $—(C_nH_{2n})—$ wherein n is an integer of from 0 to 8;

Y is S, O, or N;

x is an integer from 1 to 3; and each Z is the same or different and may be H, lower alkyl, aryl, cycloalkyl, aralkyl, or halo substituted alkyl, acyl, cycloalkyl or aralkyl; and the non-toxic pharmaceutically acceptable salts thereof.

2. A steroid compound of the cholane series having a D-ring side chain structure of the formula,

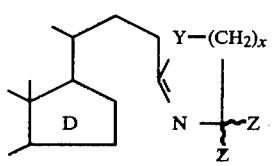

wherein Y, Z and x are as defined in claim 1.

3. A steriod compound of the pregnane, cholestane, cholane or androstane series having a D-ring side chain structure of the formula,

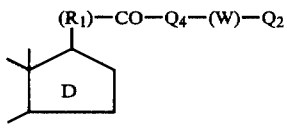

wherein $Q_4$ is NH or S;
W is

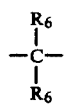

wherein each $R_6$ may be the same or different and may be H, lower alkyl, cycloalkyl, aryl, aralkyl, haloalkyl, or haloaryl; and $Q_2$ is $(CH_2)_r$—A, wherein r is an integer of from 0 to 6 and A may be —COOH, —CH$_2$OH, NH$_2$, SH or SO$_3$H; and $R_1$ is as defined in claim 1.

4. A steroid compound of the formula,

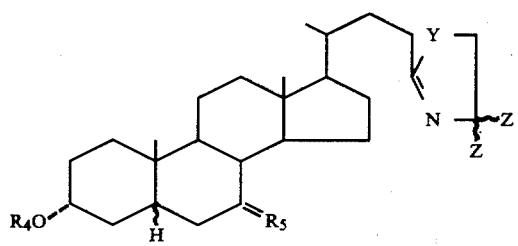

wherein $R_4$ is H, alkyl or acyl; $R_5$ may be

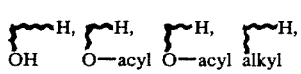

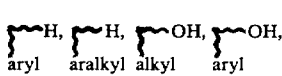

or oxo (O=); and Y is S, O or N; each Z is the same or different and may be H, OH, lower alkyl, aryl, cycloalkyl, aralkyl, aryloxy, or halo-substituted lower alkyl, aryl, cycloalkyl or aralkyl; and the non-toxic pharmaceutically acceptable salts thereof.

5. A steroid compound of the pregnane, cholestane, cholane or androstane series having a D-ring side chain structure of the formula,

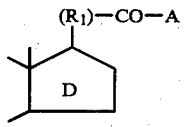

wherein A may be:
—NHCH$_2$CH$_2$OH
—NHC(CH$_2$)$_2$(CH$_2$)$_2$CH$_2$OH
—NHC(CH$_3$)$_2$CH$_2$OH
—NHC(CH$_3$)$_2$CH$_2$CH$_2$OH
—NHC(C$_6$H$_5$)$_2$CH$_2$OH
—SC(CH$_3$)$_2$CH$_2$NH$_2$
—NHC(CH$_3$)$_2$CH$_2$SH
—NHC(CH$_3$)$_2$CH$_2$NH$_2$
—NHC(CH$_3$)$_2$CH$_2$CH$_2$OH
—NHC(CF$_3$)$_2$CH$_2$OH
—NHC(C$_6$H$_{11}$)$_2$CH$_2$OH
—NHCH$_2$COOH
—NHC(CH$_3$)$_2$COOH and ($R_1$) is as defined in claim 1.

6. A steriod compound of the pregnane, cholestane, cholane or androstane series having a D-ring side chain structure of the formula:

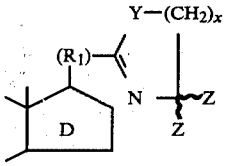

wherein
Y is S, O or N;
x is 1, 2, or 3;
Z is the same or different and is H; CH$_3$; C$_6$H$_5$; CF$_3$; or C$_6$H$_{11}$; and
($R_1$) is as defined in claim 1.

7. A steroid compound of the cholane series having a D ring side chain structure of the formula,

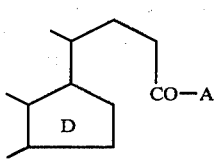

wherein A is as defined in claim 5.

8. A steriod compound of the cholane series having a D-ring side chain structure of the formula:

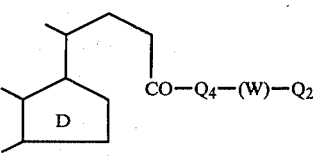

wherein $Q_4$, W, and $Q_2$ are as defined in claim 3.

9. A steroid compound of the formula,

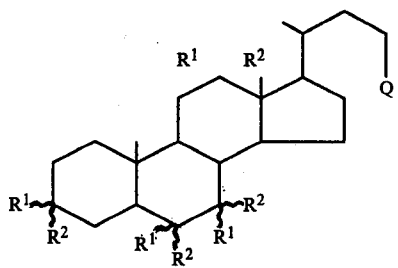

wherein
  each $R^1$ may be H, OH, alkyl, acyloxy, alkoxy or aryloxy;
  each $R^2$ may be H, OH, acyloxy, alkyl, aryl alkoxy or aryloxy; provided that only one of $R^1$ and $R^2$ may be OH, acyloxy, alkoxy or aryloxy; and
  when taken together $R^1$ and $R^2$ is oxo (O=); and Q may be

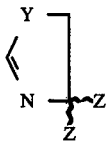

or $CO-Q_4-(W)-Q_2$
wherein
  $Q_4$ is NH or S;
  W is

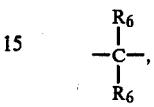

wherein each $R_6$ may be the same or different and may be H, lower alkyl, cycloalkyl, aryl, aralkyl, haloalkyl or haloaryl;
  $Q_2$ is $(CH_2)_r-A$, wherein r is an integer of from 0 to 6 and A may be —COOH, —CH$_2$OH, —NH$_2$, —SH or —SO$_3$H; and
  Y and Z are as defined in claim 4; and the nontoxic pharmaceutically acceptable salts thereof.

* * * * *